United States Patent [19]

Okada

[11] 4,196,202

[45] Apr. 1, 1980

[54] CARCINOSTATIC COMPOSITION CONTAINING 3-N-O-TOLUYL-5-FLUOROURACIL PRODUCING THE SAME

[76] Inventor: Taiji Okada, 26-41,, Motoujinamachi, Hiroshima, Japan

[21] Appl. No.: 862,591

[22] Filed: Dec. 20, 1977

[51] Int. Cl.² .......................................... A61K 31/505
[52] U.S. Cl. ..................................... 424/199; 424/251; 544/313
[58] Field of Search ................. 544/313; 424/199, 251

[56] References Cited

U.S. PATENT DOCUMENTS 4,088,646  5/1978  Ishida et al. ......................... 544/313

Primary Examiner—Paul M. Coughlan, Jr.

Attorney, Agent, or Firm—Armstrong, Nikaido, Marmelstein & Kubovcik

[57] ABSTRACT

Carcinostatic composition containing an oily substance such as a glyceride and 3-N-o-toluyl-5-fluorouracil suspended therein. The composition exhibits a remarkable carcinostatic effect against various cancerous cells at a low dose and has less side-effects than 5-fluorouracil and its known derivatives which have been typical carcinostatic compounds. A process of producing carcinostatic composition comprises dispersing 1,3-di-N-acyl-5-fluorouracil into an oily substance such as a glyceride to prepare an emulsion and selectively substituting a hydrogen atom only for the 1-position acyl group, whereby the compound is acylated only at the 3-position and which is a chief constituent of the carcionstatic composition.

3 Claims, 1 Drawing Figure

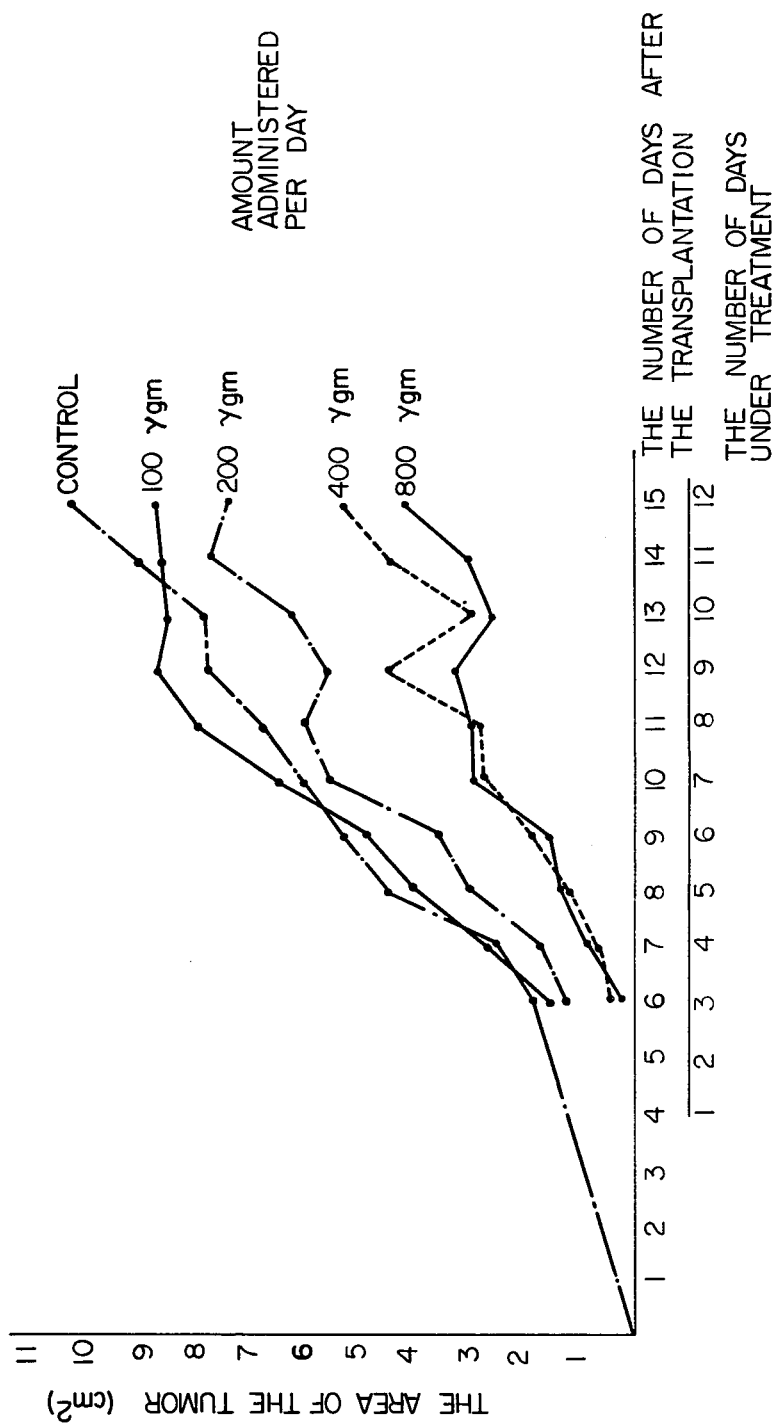

CARCINOSTATIC COMPOSITION CONTAINING 3-N-O-TOLUYL-5-FLUOROURACIL PRODUCING THE SAME

BACKGROUND OF THE INVENTION

The present invention relates to carcinostatic compounds and compositions and a process for producing the same chiefly containing 5-fluorouracil derivatives (hereinafter referred to as 5-FU). 5-FU and its various derivatives are known to act as carcinostatic agents which disrupt cancerous cells or depress the multiplication thereof. Among these derivatives, the inventor has repeated several tests including a biological test with respect to a novel substance, 1,3-di-N-o-toluyl-5-FU, and known derivative 1,3-di-N-acyl-5-FU, respectively, and revealed that their carcinostatic effects were both extremely unstable. That is to say, in spite of the fact that a remarkable carcinostatic effect was achnowledged using a low dose, a high dose sometimes leads to less carcinostatic effects than a low dose. Several studies have been concentrated on the cause of this fluctuation in the carcinostatic effect and it has been found experimentally that the composition containing 1,3-di-N-acyl-5-FU, itself, exhibits an inferior effect, but the composition containing the converted form of 3-N-acyl-5-FU provides a superior effect. In general, it can be easily presumed that these acylated 5-FU compounds, having the substituent group of NH, are to be obtained in acylation with the reagents represented by the general formula such as RCOX, wherein R represents an acyl group and X is halogen and $(RCO)_2O$, wherein R is an acyl group. However, 3-N-acyl-5-FU cannot be obtained directly from 5-FU because the acylation will preferably occur at the 1-position of 5-FU when 5-FU is reacted with the reagents under normal conditions. Conventionally, 3-N-acyl-5-FU was obtained by removing 1-position acyl group in a special manner from 1,3-di-N-acyl-5-FU that has been prepared temporarily by reacting with excess reagents mentioned above; however, the compound obtained by this conventional process will hydrolyze immediately in the body before reaching a cell, resulting in reduced carcinostatic effects.

It is a primary object of the present invention to provide carcinostatic compounds and compositions capable of being absorbed stably in the body and decomposed in cancerous cells to disrupt it or inhibit the multiplication thereof.

Another object of the invention is to provide a novel process for producing the carcinostatic compounds and compositions effectively.

These and other objects of the invention will become more apparent from the detailed description and examples which follow.

SUMMARY OF THE INVENTION

The present invention is directed to a novel compound and composition, wherein the compound is 3-N-o-toluyl-5-FU. The invention is also directed to a process for preparing 3-N-acyl-5-FU compounds by (1) dispersing about 1.5 to 3% by weight of a 1,3-di-aromatic or aryl acyl-5-FU compound in a glyceride. An emulsion (2) is formed by mixing about a 2-3 wt. percent solution of glycerine in water and about 1-2 wt. percent of a phospholipid. Dispersion (1) and emulsion (2) are mixed together to form a resulting emulsion and the resulting emulsion is permitted to stand at temperatures of at least 10° C., and preferably 17°-25° C. for 10-20 days, to liberate the aromatic or aryl acyl group at the 1-position such that substantially all of the 1,3-di-N-aromatic or aryl acyl-5-FU is converted to 3-N-aromatic or aryl acyl-5-FU. The liberated aromatic or aryl acyl group forms its corresponding carboxylic acid and dissolves in the water phase. An absorbent is used to remove the carboxylic acid from the emulsion.

BRIEF DESCRIPTION OF THE DRAWINGS

The single FIGURE in the drawing is a graph indicating the carcinostatic effects of the compound and composition produced by this invention where the area of the tumor is plotted as the ordinate and the number of days as abscissa.

DETAILED DESCRIPTION OF THE INVENTION

The present invention has been completed through a number of studies with special reference to the aforementioned phenomena, and will hereinafter be described in detail.

1,3-di-N-acyl-5-FU, which is the starting material, is obtained by known acylation, i.e., by substitution of acyl group for hydrogen atoms attached to the imine group of the 1-position and the 3-position of a 5-FU, using as a reagent, for example, 2 moles or more of a halide or acid anhydride of any aromatic carboxylic acid such as benzoic acid, toluic acid, anistic acid, and nitro-benzoic acid. The 1,3-di-N-aromatic or aryl acyl-5-FU thus obtained is dissolved or dispersed in an oily substance to form a mixture.

The oily substance that may be employed is a glyceride represented by the general formula $C H RR'R''$, wherein R, R' and R'' represent saturated or unsaturated fatty acid groups such as olefin, represented by $C_3H_5(OCOC_{17}H_{33})_3$ or triolein; tripalmitin represented by $C_3H_5(OCOC_{15}H_{31})_3$; stearodiolein represented by $C_3H_5OCOC_{17}H_{35}(OCOC_{17}H_{33})_2$; and palmitooleostearin represented by $C_3H_5OCOC_{15}H_{31}.OCOC_{17}H_{33}.OCOC_{17}H_{35}$.

An emulsion is prepared by adding about 1-2 wt. percent of a phospholipid as a stabilizer in water. The phospholipids which may be employed include (1) lecithin represented by the structural formulas:

$H_2C—O—COR;$ $H—C—O—COR;$ and $H_2C—O—PO_2H—OCH_2CH_2NOH(CH_3)_3$ wherein R and R' represent palmitic acid, stearic acid, oleic acid, linoleic acid or arachidonic acid, or phosphatidic acid which is represented by the structural formulas:

| $H_2C—O—COR;$ | $H_2C—O—COR;$ |
| --- | --- |
| $H—C—O—COR';$ | $H—C—O—PO_3H_2;$ and |
| $H_2C—O—PO_3H_2;$ | $H_2C—O—COR'$ | wherein R and R' represent palmitic acid, stearic acid or linoleic acid.

About 4-6 wt. percent of the mixture of said 1,3-di-N-acyl-5-FU and about 96-94 Vol. percent of the oily substance is added to the emulsion containing water and the stabilizer to make a second emulsion. This emulsification can be attained by subjecting the emulsion to ultrasonic treatment for about 20 minutes and also by shaking or stirring. As a result, the 1,3-di-N-acyl-5-FU appears to be dispersed in the emulsion. The resulting emulsion is permitted to stand at a temperature of at least 10° C. for 10–20 days (preferably, for at least one week), causing the aryl acyl group of the 1-position to liberate as an aromatic carboxylic acid and dissolve in the water phase. The acid thus liberated and dissolved in water phase is removed with an absorbent as necessary to prepare a carcinostatic composition chiefly composed of 3-N-acyl-5-FU, which may be administered orally, either directly or in a liquid preparation or, preferably, in an oil emulsion. Upon the removal of said liberated acid, suitable alkali such as sodium bicarbonate and the like may be added to neutralize and absorb it in the form of aromatic carboxylate, whereby it can be readily removed from the emulsion phase.

As an absorbent, finely divided decolorized carbon with a large active surface, such as that sold under the tradename "NORIT", are preferred, but other surface-active agents capable of absorbing acids or salts may be utilized.

The carcinostatic composition prepared by this invention is to be administered orally in the form of an emulsion and exhibits distinguished carcinostatic effects against tumors and adenocarcinoma, as is frequent in stomach cancer or in the part of lung cancer, and epidernoiccarcinoma, which is common to lung cancer. In addition, the composition has many other advantageous features, e.g., only a low dose is necessary to be effective so that harmful side-effects are avoided as regards the normal cells. Although it is not completely understood as to the exact mechanism by which the emulsion, chiefly composed of 3-N-acyl-5-FU, exhibits the carcinostatic effect, the 3-N-acyl-5-FU is believed to be absorbed in the body without decomposing and reaches a cancerous cell, at which time the 3-position acyl group is liberated to become a hapten, which is then converted into a new antigen. This antigen induces a specific immunoreaction against cancer due to an antigen-antibody reaction, whereby the cancerous cell will be disrupted. Furthermore, it is believed that the 5-FU ring is readily incorporated into RNA as a substituent for uracil. That is, because of the substitution of bromine for the 5-position hydrogen atom of uracil, 5-FU is incorporated into RNA and acts like cytosine, rather than uracil, to block thymidylate synthetase as well as to initiate misprint and thus depress the multiplication of cancerous and tumorous cells and consequently destroy the cells. It was confirmed experimentally that this depressing-and-destroying effect acted selectively on cancerous and tumorous cells, but substantially avoided any effects on normal cells.

As described hereinbefore, this invention, by selecting 1,3-di-N-acyl-5-FU as a starting material and substituting hydrogen for the 1-position of the starting material, makes possible the feasible preparation of the compound acylated only at the 3-position, the effective constituent of carcinostatic compounds. It would be extremely difficult to obtain such compounds by the acylation of 5-FU since, according to the present invention, 1,3-di-N-acyl-5-FU is dispersed into an oily substance to prepare an emulsion which is permitted to stand for several days, the resulting emulsion becoming stable without liberating the 3-position acyl group.

EXAMPLE 1

Fifty (50) mg of 1,3-di-N-o-toluyl-5-FU were completely dissolved in 2.5 ml of triolein at about 80° C. to form a solution. An emulsion was prepared by adding 0.6 ml of lecithin, derived from an egg, to a mixture of 1.25 g of glycerin and 45.9 ml of water. Supersonic waves were applied to the mixture to prepare an emulsion (1). Emulsion (1) was mixed together with the solution of 1,3-di-N-o-toluyl-5-FU dissolved in triolein and the resulting mixture was subjected to supersonic wave treatment for about 20 minutes so as to prepare an emulsion (2). Emulsion (2) was permitted to stand at ordinary temperatures for two weeks to produce a carcinostatic composition for oral administration chiefly composed of 3-N-o-toluyl-5-FU. As a result of the reaction, almost 100% of the 1-position o-toluyl groups were substituted by hydrogen atoms.

EXAMPLE 2

The following tests were conducted to confirm the carcinostatic effects using the produced carcinostatic composition in a pharmaceutical form of emulsion.

Ehrich cancerous cells were incubated to be dispersed by a definite number in a medium. Carcinostatic compositions having different concentrations were administered to the cells and, 72 hours after the administration, the formation of the colony was investigated. The test was conducted as follows:

0.5 ml of serum was pipetted onto several Farcon plates and 1 ml of the 3-N-o-toluyl-5-FU oil emulsion, which was prepared in graded concentrations ranging from 0.125 $\gamma$/ml to 2.0 $\gamma$/ml, was also added to the plates. The 1 ml of a medium in which Ehrich cancerous cells were cultured, so that their initial cell number would be $2 \times 10^4$ (sample 1) and $2 \times 10^3$ (sample 2), was added to each Farcon plate. Finally, 3% of agar solution prepared in a medium and maintained at 50° C. was added to each Farcon plate and incubated in a $CO_2$ incubator for 3 days, after which the total number of colonies formed on the Farcon plate were counted. As a medium for the Ehrich cancerous cells, a 10% serum designated MES $S_{10}$ and having the following composition was used, in 1 liter (9.3 g):

| | |
|---|---|
| sodium chloride | 6.800 g |
| potassium chloride | 0.400 g |
| sodium dihydrogenphosphate (anhydride) | 0.115 g |
| magnesium sulphate (anhydride) | 0.0935 g |
| calcium chloride (anhydride) | 0.200 g |
| dextrose | 1.00 g |
| L-arginine hydrochloride | 0.126 g |
| L-cystine | 0.024 g |
| L-histidine hydrochloride (monohydrate) | 0.042 g |
| L-tyrosine | 0.036 g |
| L-isoleucine | 0.052 g |
| L-leucine | 0.052 g |
| L-lysine hydrochloride | 0.073 g |
| L-methionine | 0.015 g |
| L-phenylalanine | 0.032 g |
| L-threonine | 0.048 g |
| L-tryptophane | 0.010 g |
| succinic acid | 0.075 g |
| L-valine | 0.046 g |
| sodium succinic | 0.100 g |
| chloine bitartrate | 0.0018 g |
| folic acid | 0.001 g |
| i-inositol | 0.002 g |
| nicotinamide | 0.001 g |
| calcium pantothenicate | 0.001 g |

| | -continued | |
|---|---|---|
| pyridoxine hydrochloride | | 0.001 g |
| riboflavin | | 0.0001 g |
| thiamine hydrochloride | | 0.001 g |
| biotin | | 0.00002 g |

OTHER ADDITIVES:

| | | |
|---|---|---|
| L-glutamine (sterilized by filtration) | | 0.292 g |
| 10% sodium bicarbonate aqueous solution (high-pressure hermetical sterilization) | | approximately 12 ml (1.2 g) |

Table 1

The results are tabulated in Table 1:

| the amount of administration | the number of colonies formed | | the ratio of | |
|---|---|---|---|---|
| (Γ/ml) | Sample 1 | Sample 2 | colony formation | S % |
| 0(Control) | 20412 | 1276 | 0.83 | 100 |
| 2.0 | 0 | 0 | 0 | 0 |
| 1.0 | 0 | 0 | 0 | 0 |
| 0.5 | 0 | 0 | 0 | 0 |
| 0.25 | 3098 | 729 | 0.26 | 31 |
| 0.125 | 10206 | 729 | 0.44 | 53 |

In Table 1, the initial number of cells in Sample 1 is about $2 \times 10^4$ and that of Sample 2 is about $2 \times 10^3$. S is the ratio of the number of colonies formed in the treated cells to that in the untreated ones, and expressed as percentage of representation.

EXAMPLE 3

Ehrich tumors were transplanted in an ICR strain of mice and, three days after the transplantation, a definite dose of said carcinostatic composition was administered each day for 14 days to observe the multiplication of the cells, the results of which are shown in the attached FIGURE, in which the area (cm²) of the tumor is plotted as the ordinate and the number of days as the abscissa. This FIGURE proves that the multiplication of the cells in the tumor is depressed to a greater extent with increasing doses of the composition, as compared with that of the Control to which the composition was not administered.

EXAMPLE 4

After a definite amount of Ehrich cancerous cells were transplanted to the same kind of mice as employed in the above EXAMPLE 2, the carcinostatic composition was administered at a definite dose each day for fourteen consecutive days to investigate the efficacy of the composition, the results of which are tabulated in Table 2.

Table 2

| Dose | | | | | |
|---|---|---|---|---|---|
| dose per day (γ gm) | gross doses (mg) | number of mice | interpretation | tumor weight (g) | ratio of tumor |
| 0(Control) | 0 | 10 | — | 6.02 ± 1.51 | 1.000 |
| 800 | 11.200 | 10 | Effective P = 0.01 | 1.43 ± 1.35 | 0.237 |
| 400 | 5.600 | 10 | Effective P = 0.05 | 3.35 ± 1.63 | 0.556 |
| 200 | 2.800 | 10 | Invalid | 5.06 ± 2.01 | 0.840 |
| 100 | 1.400 | 10 | Invalid | 5.78 ± 2.20 | 0.960 |

In Table 2, the dose per day and the gross dose (total amount administered over 14 days) is the amount administered to each mouse, respectively. The ratio of tumor is the weight ratio of the treated tumor to that of the Control which was untreated, and the interpretation was done by statistical analysis with a computer to determine the efficacy of the composition. That is, P=0.01 represents that the dose may not be effective for 1% of the mice, but can be effective for 99%. Consequently, it is clear from Table 2 that remarkable carcinostatic effects can be expected when more than 400 γgm per day are administered to the mouse.

Such results are further supported by the graph in the FIGURE, wherein it is shown that amounts of more than 400 γgm/day are effective.

EXAMPLE 5

To further show the advantageous effects of 3-N-o-toluyl-5-FU of the present invention over related compounds known in the art, such as FT-207 and 5-FU, tests were conducted in accordance with the procedures as described below and the results are presented in Tables 3 and 4.

The formulas for the tested compounds are as follows:

3-N-o-toluyl-5-FU

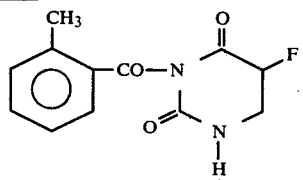

FI-207

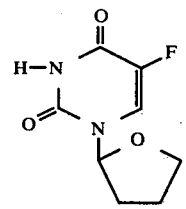

5-FU

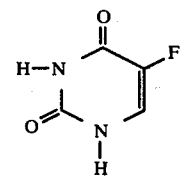

(1) METHOD

Mice were separated into 7 groups of 10 mice. Sarcoma 180, having an initial cell number of $5 \times 10^5$, was innoculated hypodermically into each subject. After 24 hours, each composition was given to the subject mouse, except the Control, at the dose as shown in Table 3 for seven (7) consecutive days. On the tenth day from the initial innoculation, each subject was anatomized to examine the tumor weight, the average of which was then compared with that of the Control. Toxicity was also interpreted in view of general debility, decrease in weight and napping. In this test, 3-N-o-toluyl-5-FU was administered orally in the form of powder mixed with water, which was isolated by chromatography from that in oil emulsion. The results are given in Table 3 below:

Table 3

Carcinostatic effect against Sarcoma 180 (of a mouse)

| compound | dose (mg/kg) daily | total | ratio of tumor in wt. | toxicity |
|---|---|---|---|---|
| FT-207 | 100 | 700 | 0.516 | − |
|  | 200 | 1400 | 0.418 | + |
| 5-FU | 10 | 70 | 0.840 | − |
|  | 30 | 210 | 0.540 | + |
| 3-N-o-toluyl-5-FU | 50 | 350 | 0.550 | − |
|  | 100 | 700 | 0.367 | − |
| Control | − | − | 1.00 |  |

(2) METHOD

Rats were separated into 7 groups of 10 rats. AH 130, having an initial cell number of $5 \times 10^5$, was injected hypodermically into each subject and, after 24 hours, each composition was given to each subject rat at the dose shown in Table 4 for seven (7) consecutive days. On the 10th day from the initial innoculation, each subject was anatomized to examine the tumor weight, the average of which was compared with that of the non-treated Control. In this test, 3-N-o-toluyl-5-FU was also administered orally in the form of powder as in the former test. The results are shown in Table 4 below:

Table 4

Carcinostatic effect against AH 130 (tumor cells of liver cancer of a rat)

| Compound | does (mg/kg) daily | total | ratio of tumor in wt. | toxicity |
|---|---|---|---|---|
| FT-207 | 90 | 630 | 0.60 | − |
|  | 200 | 1400 | 0.35 | + |
| 5-FU | 10 | 70 | 0.72 | − |
|  | 30 | 210 | 0.55 | + |
| 3-N-o-toluyl-5-FU | 30 | 210 | 0.84 | − |
|  | 100 | 700 | 0.35 | − |
| Control | − | − | 1.00 |  |

As illustrated in Tables 3 and 4, from the relation between the amount of composition administered and the ratio of the tumor, it has been shown that an effective disruption of the cancerous cells or depression of the multiplication thereof is increased as the amount administered is increased for all drugs as above. However, it is important to note that, for FT-207 and 5-FU, increasing the amount of the compound administered produces toxic results as indicated by the "+" in the Table under "Toxicity", which indicates the production of side-effects; while for 3-N-o-toluyl-5-FU of present invention, this compound does not produce toxic side-effects as the amount of administration increases while providing a lower tumor ratio. That is, the use of 3-N-o-toluyl-5-FU provides the advantageous result of using increasing amounts of the compound to provide carcinostatic effects without providing toxic side-effects.

EXAMPLE 6

Included in Tables 5 through 7 for comparison are carcinostatic effect of 3-N-o-toluyl-5-FU on various kinds of cancerous cells. In these tables, MIC represents minimum inhibitory concentration ($\gamma$ or microgram/ml) required to inhibit the growth of cancerous cells in a culture medium and $ED_{50}$($\gamma$ or microgram/ml) represents the dose per unit volume effective for 50% of the cells.

METHOD

Cancerous cells employed:
(1) Ehrich cancerous cells of mouse;
(2) Human thyroid cancerous cells; and
(3) Leiomyosarcoma cells of human.

Each kind of said cancerous cells, having an initial number of $3 \times 10^4$ and $4 \times 10^4$ was cultured in a nutrient medium on a slide glass in a flat bottle for 24 hours to make more than one sample, respectively; half for 5-FU and the other for 3-N-o-toluyl-5-FU in oil emulsion. Then 5-FU diluted with water of different concentrations and 3-N-o-toluyl-5-FU in oil emulsion of different concentrations was respectively added to the cells of each of said plate to make several different concentrations of said compounds per unit volume of each cell, and the culture was continued for three days. The manner of the action of each of said compounds against each of the cells at different concentrations (weight per unit volume of cell) was observed by an inverted phase contrast microscope with the passage of time, as well as the multiplication and the change in morphology of the cells were examined by fixing and staining the cells on the slide glass after a period of three days. As a nutrient medium, MEM $S_{10}$ or HAM-F $S_{10}$ was employed. HAM-F $S_{10}$ is a 10% serum supplemented medium described by Richard G. Ham in 1964, and is sold under the tradename "HAM $F_{12}$ Nissui" in Japan.

Its composition is as follows:
In 1 liter (10.8 g):

| | |
|---|---|
| sodium chloride | 7599.0 mg |
| potassium chloride | 224.0 mg |
| sodium monohydrogenphosphate (heptahydrate) | 268.0 mg |
| copper sulphate (pentahydrate) | 0.002 mg |
| zinc sulphate (heptahydrate) | 0.9 mg |
| ferrous sulphate (heptahydrate) | 0.8 mg |
| magnesium chloride (hexahydrate) | 1.220 mg |
| calcium chloride (dihydrate) | 44.0 mg |
| dextrose | 1802.0 mg |
| L-arginine hydrochloride | 211.0 mg |
| L-alanine | 9.0 mg |
| L-asparagine | 13.0 mg |
| L-asparatic acid | 13.0 mg |
| L-cysteine hydrochloride | 32.0 mg |
| L-glutamic acid | 15.0 mg |
| L-glutamine | 146.0 mg |
| glycine | 8.0 mg |
| L-histidine hydrochloride | 19.0 mg |
| L-isoleucine | 4.0 mg |
| L-leucine | 13.0 mg |
| L-lysine hydrochloride | 37.0 mg |
| L-methionine | 4.0 mg |
| L-phenylalanine | 5.0 mg |
| L-proline | 35.0 mg |
| L-serine | 11.0 mg |
| L-threonine | 12.0 mg |
| L-tryptophane | 2.0 mg |
| L-tyrosine | 5.0 mg |
| L-valine | 12.0 mg |
| biotin | 0.007 mg |
| choline chloride | 14.0 mg |
| calcium pantothenicate | 0.5 mg |
| folic acid | 1.0 mg |
| hypoxanthine | 4.0 mg |
| purtescine dihydrochloride | 0.3 mg |
| inositol | 18.0 mg |

| -continued | |
| --- | --- |
| pyridoxine hydrochloride | 0.06 mg |
| riboflavin | 0.04 mg |
| sodium pyruvicate | 110.00 mg |
| thiamine chloride | 0.3 mg |
| thymidine | 0.7 mg |
| cyanocobalamine | 1.0 mg |

The molecular weight of 5-FU is about 130 and that of 3-N-o-toluyl-5-FU is about 248. Therefore, for the same weight concentration of each compound, the number of molecules of 3-N-o-toluyl-5-FU will be about one-half that of 5-FU. Accordingly, as used in the following explanations, the terms "weight concentration" refers to the $\gamma gm/ml$ of each compound used in a given test, and the term "molarity" generally refers to the number of molecules of each compound present in a given amount used in a test. As stated above, in the same weight concentration of each compound, the "molarity" of 3-N-o-toluyl-5-FU will always be about one-half that of 5-FU.

(a) The samples as prepared above were tested on Ehrich cancerous cells of mice and the results are shown in Table 5:

Table 5

| | MIC | $ED_{50}$ |
| --- | --- | --- |
| 5-FU | 2.5 | 1.0 |
| 3-N-o-toluyl-5-FU | 2.0 | 1.0 |

The conclusion reached from Table 5 is that, even though $ED_{50}$ of the compound of the present invention is the same as that of 5-FU, the former is superior to the latter because (taking the number of molecules as a reference standard), the number of molecules of the compound of the invention is half that of 5-FU for $ED_{50}$, and for MIC the compound of the invention is apparently superior to 5-FU in both weight concentration and molarity (the number of molecules).

EXAMPLE 7

The samples as prepared in EXAMPLE 6 were tested on human thyroid cancer cells and the results are shown in Table 6.

Table 6

| | MIC | $ED_{50}$ |
| --- | --- | --- |
| 5-FU | 2.5 | 1.25 |
| 3-N-o-toluyl-5-FU | 1.25 | 0.6 |

As is clear from Table 6, the compound of the invention exhibits carcinostatic effects at less than half the dose in weight concentration than that of 5-FU.

EXAMPLE 8

The samples as prepared in EXAMPLE 6 were tested on leiomysarcoma cells of mice and the results are shown in Table 7:

Table 7

| | MIC | $ED_{50}$ |
| --- | --- | --- |
| 5-FU | 2.5 | 1.25 |
| 3-n-o-toluyl-5-FU | 1.25 | 0.3 |

As to weight concentration, Table 7 shows that the compound of the invention is considerably superior to 5-FU in carcinostatic efficacy. The same superior results are observed when considering the molarity.

EXAMPLE 9

Using the same procedures as in Examples 6–8, it was investigated whether the compound of the invention causes side-effects on normal cells. Table 8 shows the MIC and $ED_{50}$ of 5-FU and 3-N-o-toluyl-5-FU, respectively, for mouse foot pad cells chosen as normal cells.

Table 8

| | MIC | $ED_{50}$ |
| --- | --- | --- |
| 5-FU | 10.0 | 2.5 |
| 3-N-o-toluyl-5-FU | 10.0 | 2.5 |

Considering that, although the minimum inhibitory concentration (MIC) for the Ehrich cancerous cell, which will require a relative high dose, is 2.5 $\gamma gm/ml$ and is equal to $ED_{50}$ for the normal cell, MIC of 3-N-o-toluyl-5-FU for Ehrich cancerous is 2.0 $\gamma gm/ml$ and is less than $ED_{50}$ for the normal one. Consequently, 3-N-o-toluyl-5-FU is proved to have less side-effects than 5-FU.

To investigate the advent of immunity, tumor cells were transplanted into the back of a mouse. After the lapse of 3 days, 3-N-o-toluyl-5-FU of difference concentration were applied to them every day for two weeks by ascites injection. Three days after the injection, the spleen was taken out to be inspected. It was found that the spleen extracted from the mouse to which 3-N-o-toluyl-5-FU was applied weighted 2 to 5 times than of a mouse to which it was not applied. This indicates the appearance of immunity resulting from invigoration of lymphatic tissue due to the administration of 3-N-o-toluyl-5-FU.

Table 9

| | $ED_{50}$ (normal cells) ($\gamma/ml$) | MIC (Elrich cancerous cells $\gamma/ml$) | MIC (human thyroid cancerous cells) | MIC (leiomy-sarcoma) |
| --- | --- | --- | --- | --- |
| 5-FU | 2.5 | 2.5 | 2.5 | 2.5 |
| 3-N-o-toluyl-5-FU in oil emulsion | 2.5 | 2.0 | 1.25 | 1.25 |

$ED_{50}$ for normal cells mean that this dose will inhibit the normal propagation of 50% of unattacked cells (that is, it may cause a harmful influence upon normal cells), while MIC for cancerous cells means that this dose will inhibit the multiplication of 100% of cancerous cells. Consequently when MIC of a compound for cancerous cells exceeds $ED_{50}$ of the same for normal cells, it is considered that this compound must have side-effects.

Turning to the figures in Table 9, for normal cells, both the compound of the invention and 5-FU have the same $ED_{50}$ (2.5 $\gamma/ml$), while for cancerous cells, for example Ehlrich cancerous cells, MIC of the latter is 2.5 $\gamma/ml$, which is equal to $ED_{50}$ of the same for normal cells. This shows that 5-FU exerts harmful influence upon 50% of the normal cells at the minimum dose required to inhibit the multiplication of the cancerous cells. On the other hand, MIC of the compound of the invention is 2.0 $\gamma gm/ml$ even for Ehlrich cancerous cells, which requires the highest dose among the others, and this dose is less than $ED_{50}$ of the same for normal cells. In short, the dose of the compound of the invention at which all the cancerous cells cease to propagate is less than $ED_{50}$ for the normal cells, while the dose of 5-FU required to inhibit the multiplication of the cancerous cells is equal to the dose at which 50% of the normal cells will be damaged. It is known from this standpoint of view that the dose of the compound of the invention effective to 100% of the cancerous cells is administered to the normal cells, the ratio of damaged cells to undamaged ones must be less than 50%, which shows that the compound of the invention has less side-effects than 5-FU.

Obviously many modifications and variations of the invention as hereinbefore set forth may be made without departing from the spirit and scope thereof.

What is claimed is:

1. A process for producing a composition containing 3-N-o-toluyl-5-FU which comprises the steps of:
    (a) dispersing 1,3-di-N-o-toluyl-5-FU in a glyceride selected from the group consisting of triolein, tripalmitin, stearodiolen and palmitooleostearin,
    (b) forming an emulsion containing water and a phospholipid,
    (c) adding the mixture of (a) to the emulsion of (b) to form a resulting emulsion,
    (d) permitting the resulting emulsion to stand at temperatures sufficient to liberate the toluyl group at the 1-position such that substantially all of the 1,3-di-N-o-toluyl-5-FU is converted to 3-N-o-toluyl-5-FU, and
    (e) removing the liberated toluyl group from the resulting emulsion.

2. The process according to claim 1 wherein the phospholipid is selected from the group consisting of lecithin and phosphatidic acid.

3. The emulsion produced according to steps (a)–(e) of claim 1.

* * * * *

UNITED STATES PATENT AND TRADEMARK OFFICE
CERTIFICATE OF CORRECTION

PATENT NO. : 4,196,202
DATED : April 1, 1980
INVENTOR(S) : TAIJI OKADA

It is certified that error appears in the above-identified patent and that said Letters Patent are hereby corrected as shown below:

In column 3, lines 29-30, correct the spelling of "epidermoiccarcinoma";

line 46, correct "bromine" to --fluorine--.

In column 9, line 57, correct the spelling of "leiomyosarcoma".

Throughout the specification, correct the word "Ehrich" to --Ehrlich--.

*Signed and Sealed this*

*Fifteenth* Day of *July 1980*

[SEAL]

*Attest:*

SIDNEY A. DIAMOND

*Attesting Officer*   *Commissioner of Patents and Trademarks*